US006300138B1

(12) United States Patent
Gleason et al.

(10) Patent No.: US 6,300,138 B1
(45) Date of Patent: Oct. 9, 2001

(54) METHODS FOR CONDUCTING TESTS

(75) Inventors: Paul J Gleason, Laguna Niguel; Robert D Miller, Costa Mesa; Rex O Bare, Lake Forest; Vijay K. Mahant, Murrieta; Christopher C Feistel, Laguna Beach; Glenn D. Walker, La Habra Heights, all of CA (US)

(73) Assignee: Qualigen, Inc., Carlsbad, CA (US)

( * ) Notice: Subject to any disclaimer, the term of this patent is extended or adjusted under 35 U.S.C. 154(b) by 0 days.

(21) Appl. No.: 09/272,234

(22) Filed: Mar. 18, 1999

Related U.S. Application Data

(63) Continuation-in-part of application No. 08/905,261, filed on Aug. 1, 1997.

(60) Provisional application No. 60/095,193, filed on Aug. 3, 1998.

(51) Int. Cl.[7] .................... G01N 33/48

(52) U.S. Cl. .................... 436/165; 436/164; 436/166; 436/177; 436/179; 436/808; 422/61; 422/102; 422/103

(58) Field of Search .................... 422/56, 58, 61, 422/100, 102, 103; 436/164, 165, 176, 177, 179, 180, 166, 808

(56) References Cited

U.S. PATENT DOCUMENTS

| | | | | |
|---|---|---|---|---|
| 3,036,894 | * | 5/1962 | Forestiere | 422/61 |
| 4,065,263 | * | 12/1977 | Woodbridge | 422/61 |
| 5,254,479 | * | 10/1993 | Chemelli | 436/180 |
| 5,422,271 | * | 6/1995 | Chen et al. | 422/58 |

* cited by examiner

*Primary Examiner*—Lyle A. Alexander
(74) *Attorney, Agent, or Firm*—Fish & Associates, LLP; Robert D. Fish

(57) ABSTRACT

Methods and apparatus for automated sample analysis are provided in which a plurality actuators are involved in moving a samples from one compartment to another, and appropriate reactants are combined with the sample in one or more of the compartments. The actuators are preferably contained in a device that also has a detector, data reduction capabilities, and a printer. Contemplated signal detectors include a photomultiplier tube, a photodiode, and a charge-coupled device. Steps contemplated to be performed automatically include aliquoting the sample, diluting the sample, contacting at least a portion of the sample with a reagent having a substantially selective binding towards the analyte. Contemplated reactants include sense and antisense nucleic acids, antibodies and antigens, solid-phases such as paramagnetic beads, reagents, other substrates, and wash solutions.

22 Claims, 6 Drawing Sheets

200

METHODS FOR CONDUCTING TESTS

This application claims the benefit of U.S. provisional application number 60/095193, filed Aug. 3, 1998, and is a continuation in part of U.S. utility application number 08/905261, filed Aug. 1, 1997, which are both incorporated herein by reference in their entirety.

FIELD OF THE INVENTION

The field of the invention is diagnostics.

BACKGROUND OF THE INVENTION

In recent decades, advances in modem chemistry and more sophisticated instrumentation have led to a plethora of clinical tests. However, the equipment and the trained personnel needed to perform such tests led also to an increase in costs. To cut down on the costs related to clinical diagnosis, many physicians frequently outsource testing of blood and other specimens to centralized or specialized laboratories. Outsourcing clinical diagnostics, however, often increases the time between acquiring a sample and obtaining a test result. A delay in obtaining a test result is especially disadvantageous when time is a critical factor in differential diagnosis, for example, in the treatment of heart attacks, poisoning or strokes. Furthermore, a delay in obtaining test results adds to the overall cost.

The time span between acquiring a sample and obtaining a test result is not only of paramount importance in clinical diagnosis, but also in a variety of other fields. Such fields are, for example, environmental chemistry to detect a source of pollution, military field tests to detect poisonous gases, or criminological investigation to find traces of chemical markers. Time constraints, as well as the requirement to perform diagnostic tests at the place of sample collection led to the development of compact, self-contained test systems. Such self-contained test systems may be categorized into two different classes.

The first class may be characterized as qualitative test systems. Many qualitative test systems provide all required reagents, and a sample can be analyzed without further need of instrumentation. In U.S. Pat. No. 3,726,645 to Kaezmarek et al., U.S. Pat. No. 3,713,779 to Sirago et al., and U.S. Pat. No. 3,689,224 to Agnew et al., for example, small, flat hand-held test kits are described, in which a liquid or gaseous sample reacts with reagents provided by the test kit. A color change of an indicator reveals the presence of analyte. In these test kits, manual application of pressure is usually used to move and mix reagents; and the sample. In other test systems, for example in U.S. Pat. No. 4,806,316 to Johnson et al., the sample is propelled by gravity or a pressure difference. Again, a color change indicates the presence of analyte. In a further example, U.S. Pat. No. 4,859,421 to Apicella, additional elements in a test kit are described, such as one-way valves that allow only unidirectional flow of reagents. Furthermore, additional reagents for positive and negative controls may be provided.

The second class may be characterized as quantitative test systems. Quantitative test systems generally require a specialized instrument, commonly a photometer or fluorimeter. Such quantitative test systems utilize various ways of detection and various ways of how the sample is moved within the test device. In U.S. Pat. No. 4,963,498 to Hillmant et al., for example, a test system is described in which a blood sample is mixed with a reagent and subsequently drawn by capillary action into a flow path. Interactions between the reagents and the sample cause a change in flow rate. The flow rate is measured using a photocell, and the change in the flow rate is then correlated with the concentration of the analyte. In another example, U.S. Pat. No. 3,799,742 to Coleman describes a test system in which a sample is placed into a small test container. The sample is then manually pushed through a filter unit into a cuvette, where a color reaction takes place. The small test container is subsequently inserted into a reading device and the concentration of the analyte is calorimetrically determined. In U.S. Pat. No. 4,673,657 to Christian, a sample is placed into an assay card and forced to a detection zone by a roller bar. A pulse vacuum may firer move the sample repeatedly over the detection zone. The detection zone may specifically bind up to 250 analytes, and the analytes can then be automatically detected and quantified via an optical or magnetic detector.

Although various quantitative and qualitative test systems are known in the art, almost all test systems have a number of disadvantages. Typically, the assays performed in such systems are single-step assays, i.e., one sample is mixed with one reagent or set of reagents, and the result of the reaction is then measured. However, many modem diagnostic reactions employ multiple steps prior to the detection reaction, for example reduction of a sample to liberate disulfide bound thiols, or coupled enzymatic reactions to indirectly measure an analyte or secondary reactions for signal amplification.

Another disadvantage of many quantitative and qualitative test systems is that reaction of a sample with a substrate, and detection of the analyte, occur in the same location. This often poses problems when additional processing steps are required after the addition of reagents to the sample. Where samples are moved from one location to another within a test system, reproducible test conditions may be difficult to achieve.

Yet another disadvantage of known quantitative and qualitative test systems is that many of them utilize squeezable containers for storage and dispensing of reagent solutions. Despite the simple operation of squeezable containers, dispensing an accurate and precise amount of a reagent from a squeezable container is often problematic. Moreover, when an accurate and precise flow rate of a reagent is needed, squeezable containers may produce inaccurate and non-reproducible results.

Yet further, while many test systems are supplied with appropriate amounts of reagents, and typically follow relatively simple protocols, a problem frequently persists in that the accuracy and precision of test results become operator i.e. technique dependent. Such measurement is therefore often prone to errors.

Thus, many test systems are known in the art to qualitatively and quantitatively determine the presence of an analyte in a sample. However, current test systems tend to limit the complexity of a reaction sequence with which an analyte can be determined. Surprisingly, despite a growing number of new and useful diagnostic systems, there is no test system that permits a relatively quick and simple detection of an analyte in a sample that requires complex test procedures, without using sophisticated instruments. Therefore, there is still a need for methods and test systems that overcomes these limitations.

SUMMARY OF THE INVENTION

The present invention provides methods and apparatus for automated sample analysis in which a plurality of actuators are involved in moving a sample from one compartment to another, and appropriate reactants are combined with the sample in one or more of the compartments.

The actuators are preferably contained in a device that also has a detector, data reduction capability, and a printer. Contemplated signal detectors include a photomultiplier tube, a photodiode, and a charge-coupled device.

Steps contemplated to be performed automatically include aliquoting the sample, diluting the sample, contacting at least a portion of the sample with a reagent having a substantially selective binding affinity towards the analyte, a buffer, an acid, a base, or a wash solution. Contemplated reactants include sense and antisense nucleic acids, antibodies, solid-phase substrates, chromophores, and amplifiers.

Various objects, features, aspects and advantages of the present invention will become more apparent from the following detailed description of preferred embodiments of the invention, along with the accompanying drawings in which like numerals represent like components.

DETAILED DESCRIPTION

Figure 1:
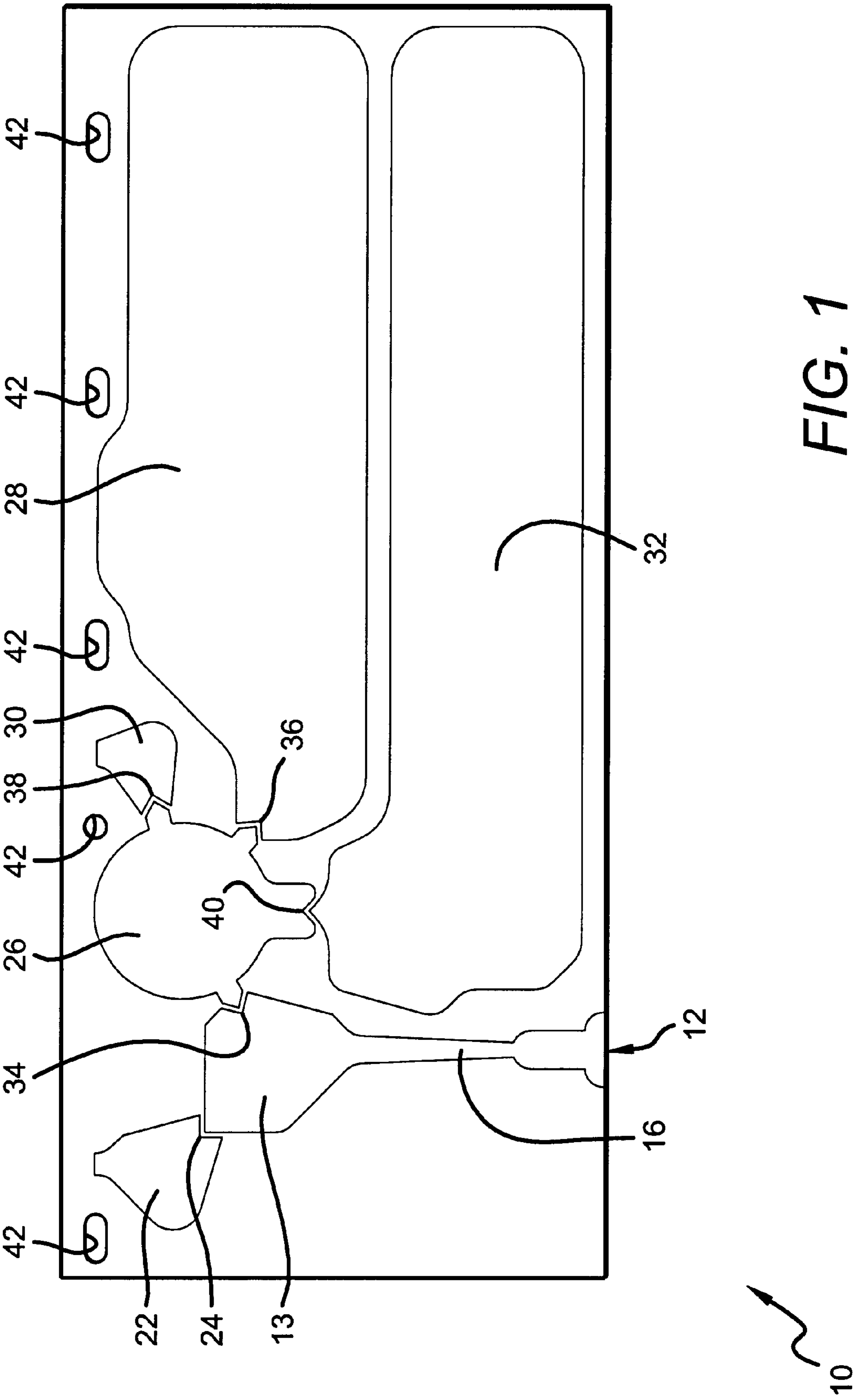
FIG. 1 is a plan view of a disposable diagnostic container according to the present invention.

FIG. 1 is a plan view of a disposable diagnostic container 10 according to the inventive subject matter, generally comprising a pouch having a sample inlet port 12, a plurality of compartments 13, 22, 26, 28, 30, and 32, as well as passageway 16 coupling the inlet port 12 with compartment 13, and portals 24, 34, 36, 38 and 40 interconnecting the various compartments.

Container 10 is a relatively flat, laminated plastic pouch measuring about 8.5 cm by about 19 cm, and about one millimeter thick, in which the compartments, inlet port, passageway and portals are all defined by heat sealing. The nature and dimensions of the container, arrangement of compartments and interconnections, as well as the contents of the compartments will, of course, vary from embodiment to embodiment, and those skilled in the art will recognize that the embodiment of FIG. 1 is merely exemplary of an enormous number of such possible containers.

The size of the container, for example, largely depends on the volume of reactants to be contained, although it is contemplated that practical containers will typically be sized to define a volume in the range of between 50 $\mu$L and about 5 milliliters. Suitable containers may have many different shapes, so long as the shape permits contact of at least one side of the container with a plurality of actuators. Preferred shapes are flat, envelope-like shapes, but box-like, round, hemispherical, or even spherical shapes, are also contemplated.

The opposing top and bottom sheets forming container 10 may advantageously be formed from a thermoplastic material, including polypropylene, polyester, polyethylene, polyvinyl chloride, polyvinylidene chloride, and polyurethane. Such sheets are contemplated to have a relatively uniform thickness between about 0.05 mm to about 2 mm. The opposing sheets need not be fabricated from the same materials. For example, one sheet may comprise a reflective foil, and the other sheet may comprise a transparent or translucent plastic. The use of foil can help promote temperature stability, and can serve as an additional moisture and oxygen barrier. Foil can also enhance thermal transfer from a heating source to a sample or reagent.

Preferred containers are flexible, either in whole or in part. Flexibility as characterized herein is the capability of yielding to a reasonable force by temporarily changing shape without damaging the structure or material. A reasonable force, as used herein, is a pressure, typically below 5 lb/in$^2$. For example, a preferred flat, envelope-like container is sufficiently flexible to be wrapped around an inch diameter cylindrical object without breaking or tearing the container. In another example, a portion of a container may advantageously be sufficiently flexible to displace a volume carried within that portion without rupturing the outer walls. The container may furthermore have a plurality of openings. The number of openings may vary considerably between at least one opening and twenty openings or more. Such openings may have a closing mechanism, be sealable or permanently open. Furthermore, some of the openings may be in liquid communication with each other, or may be used as a vent or an overflow. The container is furthermore characterized by having a plurality of compartments.

Container 10 also includes attachment holes 42 for mounting on alignment posts in an analyzer 400. Alternative attachment devices or methods are also contemplated, including hooks, loops and other mounting attachments coupled to the container 10 at appropriate locations. It is further contemplated that container 10 may be devoid of mounting components.

One or more labels (not shown) may also be affixed to the container 10. Labels may indicate identification marks, information relating to the type of diagnostic test being conducted, as well as patient information, test result data, or other information. The label(s) may optionally be removable, and may, for example, be removed from the container 10 to be placed in a patient's medical file, thereby eliminating the need for transferring data with attendant possibility for error.

Inlet port 12 serves as an entry point for receiving samples or other materials. Many configurations are contemplated, although it is preferable that the entry point uses some sort of common connection mechanism. For example, the entry point 12 in FIG. 1 is a female portion of a Luer lock mechanism. Alternative entry ports may be either simpler or more complex, and may contain a padding that can be punctured or pierced using a needle.

Contemplated entry points may also be placed elsewhere on a container other than as depicted in FIG. 1. For example, a suitable entry point for a solid material may be formed as a simple slot in one of the sheets forming the top or bottom of the container. Such an entry point may be well suited for receiving a relatively solid piece such as a tissue or mineral sample, and may be sealable by a flap or tape mechanism.

Compartments 13, 22, 26, 28, 30, and 32 are portions of container 10 that are fluidly separated from other portions of the container during at least some period of time. In general, compartments are separated from one another using at least one continuous element that contacts at least one of the walls of the container. For example, if the container is a cylinder, the continuous element could be a divider that is more or less perpendicular to the longitudinal axis of the cylinder, and contacts the inner circumference of the cylinder. Where the container is a flat bag, the continuous element may advantageously comprise a heat seal between opposing sides, in a form enclosing a defined space.

The volume of preferred compartments may advantageously vary between about 3% to approximately 90% of the total volume of the container. Such compartments may be filled with at sample, a reagent, or air, but the compartment may also have essentially no void volume. By way of example, compartment 22 may be designed to contain about 1 ml of a binding reactant, and wash compartment 28 may be designed to hold up to about 5 ml of a solvent solution.

At least some of the compartments may advantageously comprise a transparent portion through which a signal can be detected, or the progress of a reaction can be monitored. In such instances it may also be advantageous for an opposing surface to exhibit a reflective surface to improve signal detection. Compartments may also be shielded, for example against heat, light, or other radiation.

Compartments may have one or more openings, such as those at portals 34, 36, 38, and 40. Such openings may be in permanent liquid communication with the rest of the container, for example, by an incomplete wall surrounding the compartment. Openings may also be temporarily closed. For example, a breakable seal may form the opening, which separates the compartment from the rest of the container, until an opening force breaks the seal. Typically, the breakable seal is a chevron break point allowing a fluid to pass under about 5–15 psi. In another example, the opening comprises a one-way valve, which permits only a unidirectional flow of material when a pressure difference is applied between the ends of the valve. In yet a further example, the opening may be temporarily closed by a closing force. Typically, the closing force is delivered via a compression pad from outside the container, which effects a temporary physical separation of the compartment from the rest of the container.

Passageway 16 and portals 34, 36, 38 and 40 serve to fluidly connect various compartments and other spaces within the container, and with the external environment. The term "fluidly connect" specifically includes movement of any fluidizable composition, whether a liquid, gas, or fluidized solid. In many instances the fluid will be intended to move in a single direction only, but in other instances it may be advantageous to move at least a portion of a fluid in both forward and backwards directions.

In some cases compartments or other spaces may be separated by a barrier for a period of time, and it is contemplated that the barrier will at some point be breached. In such instances the separated compartments or other spaces are considered to be "fluidly connectable."

Figure 2:
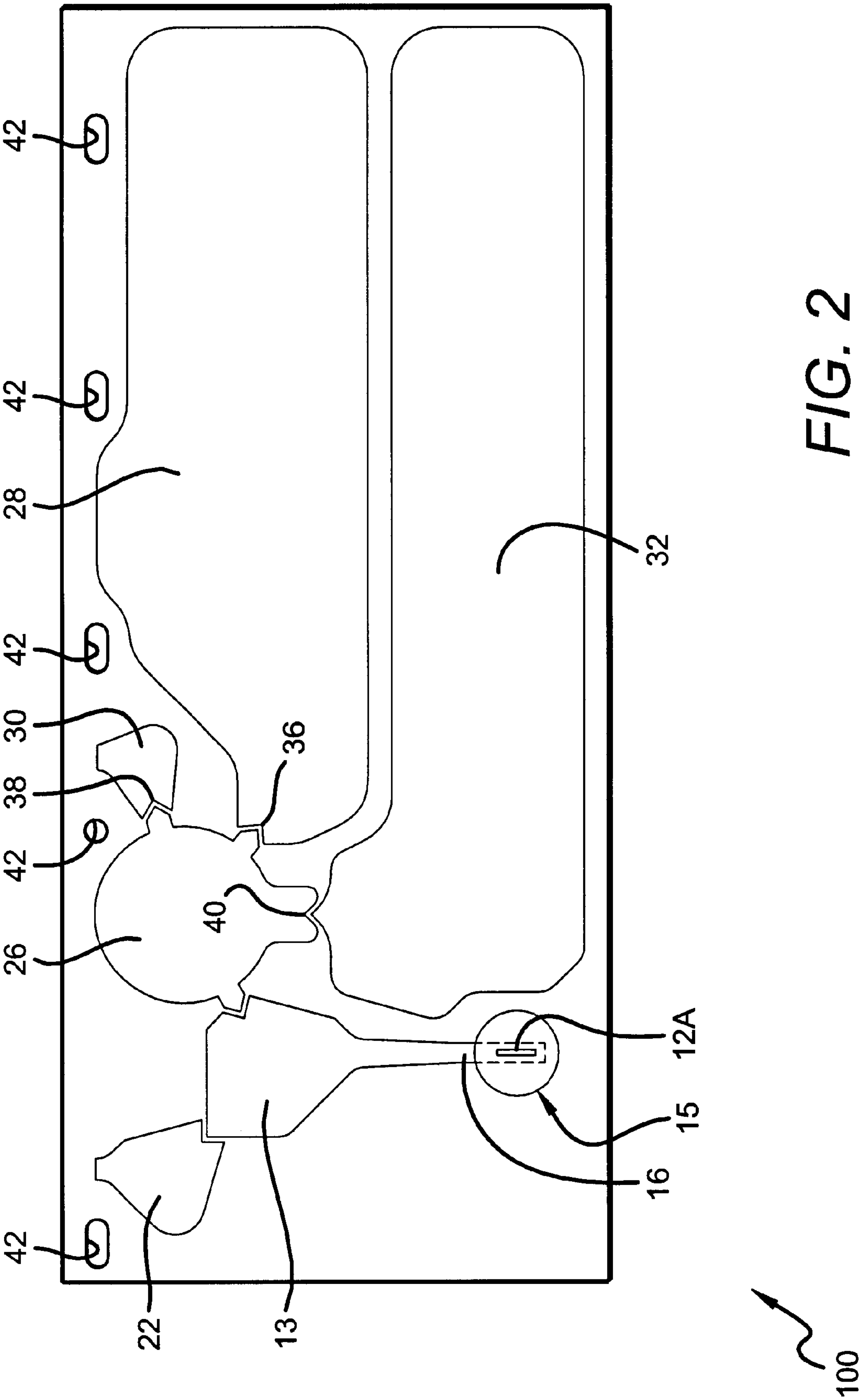
FIG. 2 is a plan view of an alternative disposable diagnostic container according to the present invention.

FIG. 2 depicts an alternative configuration in which a container 100 has an entry slot 12A instead of an entry port. The slot 12A is preferably sealable such that a liquid sample placed into container 100 does not leak out. Entry slot 12A can advantageously be located within a plastic or other ring 15. Ring 15 can be attached to the container 100 and fitted with an attachable cover (not shown) such that any liquid inserted into entry slot 12A does not leak out of the container.

Figure 3:
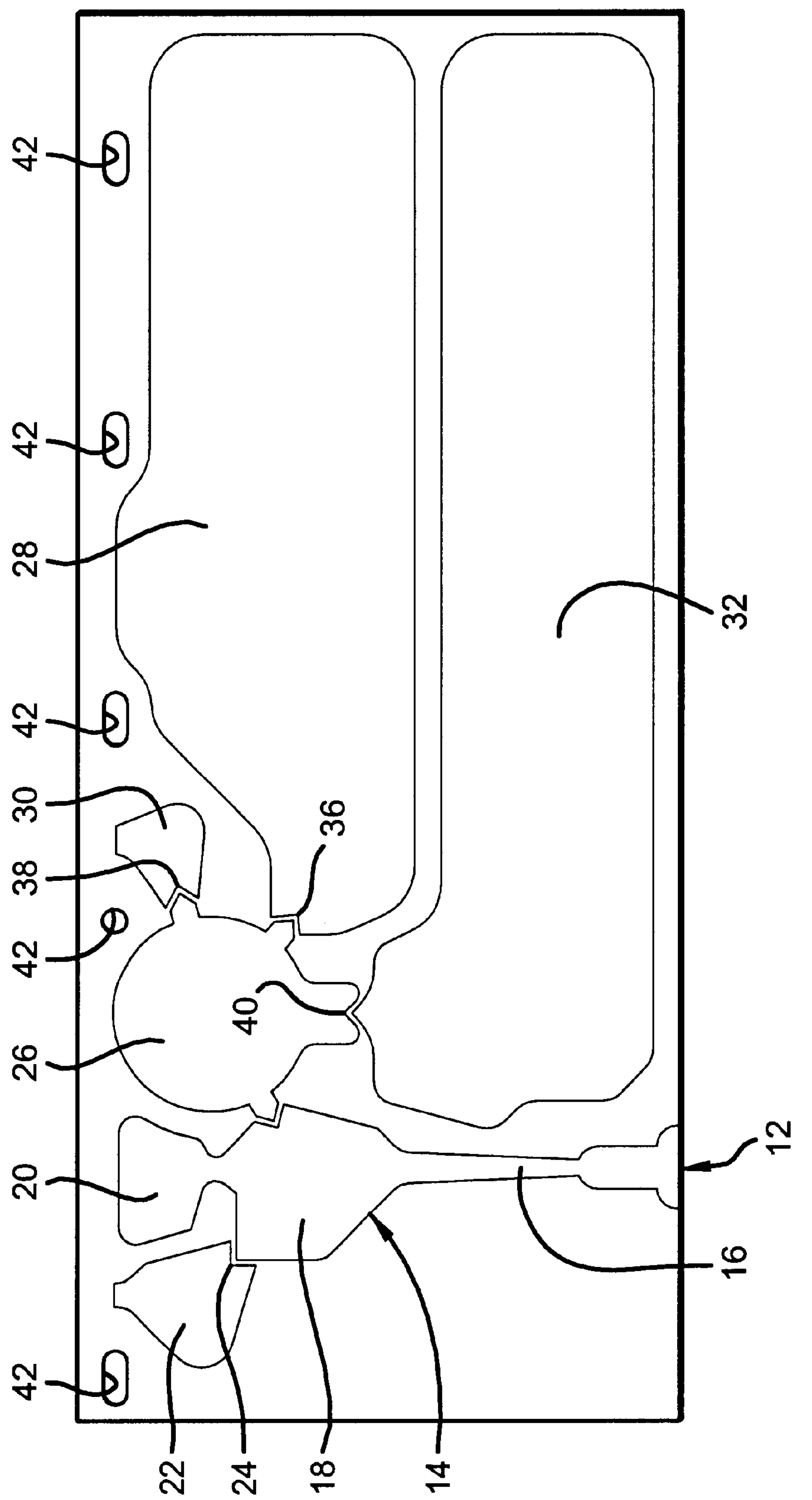
FIG. 3 is a plan view of another alternative disposable diagnostic container according to the present invention.

FIG. 3 depicts an alternative configuration in which a container 200 includes an overflow compartment fluidly coupled, or fluidly coupleable to compartment 18. Compartment 18 also contains a volumetric zone 14 that is externally partitionable to define a fixed volume to be used in a diagnostic test. For example, assuming the fixed volume is about 100 μl, fluid-receiving portion 18 can receive an input volume that is greater than about 100 μl, such as 150 μl. In this case, after receiving the 150 μl of sample, volumetric zone 14 can be externally partitioned such that the fixed volume, about 100 μl, is defined and then used for the diagnostic test with the excess volume, about 50 μl, being moved into overflow portion 20. The excess volume moved into the overflow portion would not be used in the diagnostic test since only the fixed volume of a sample typically is used to perform the diagnostic test. This externally partitionable volumetric zone 14 provides a means for quantitatively analyzing a sample.

Partitioning volumetric zone 14 typically involves two steps. The first step involves using at least one movable object such as a compression pad to apply pressure to all the areas around the region defining the fixed volume with the exception of the area providing a fluid connection to the overflow portion 20. This partially surrounds the region defining the fixed volume while allowing any excess volume to move into overflow portion 20. The second step involves using at least one movable object such as a partitioning edge to separate the excess volume from the fixed volume. This completely surrounds the region defining the fixed volume. A compression pad and partitioning edge can be made from any material provided the fixed volume can be defined. It is noted that the positioning of the movable objects can be adjusted such that the applied pressure can define any particular volume as the fixed volume.

Figure 4:
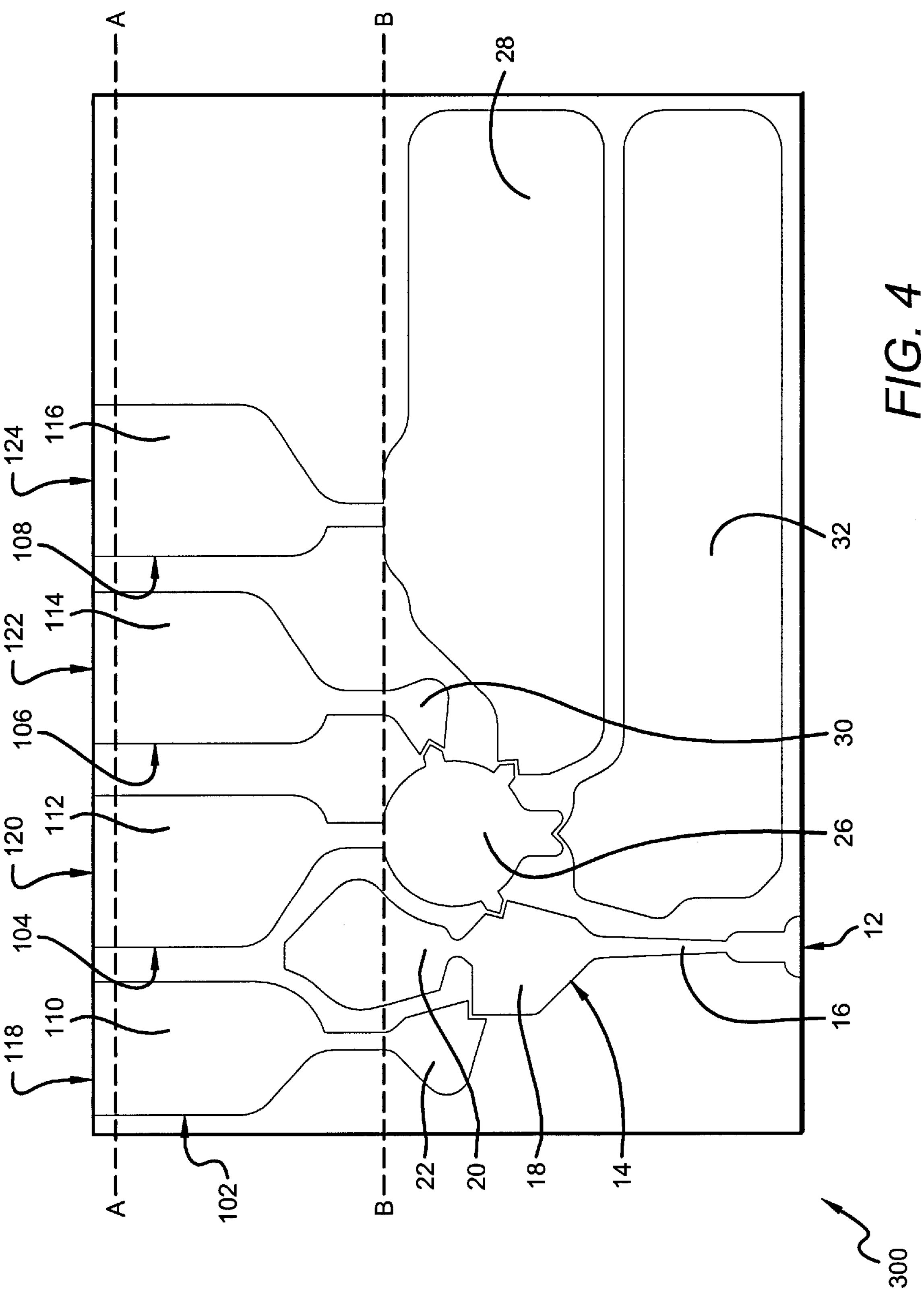
FIG. 4 is a plan view of another alternative disposable diagnostic container according to the present invention.

FIG. 4 depicts an alternative configuration in which a container 300 has additional compartments 102, 104, 106 and 108. The overflow compartment 20 depicted in FIG. 4 will have the same configuration as depicted in FIG. 3 once a seal is placed along reference line B—B. In this embodiment compartments 102, 104, 106, 108 have portions comprising reagent compartment 22, reaction compartment 26, substrate compartment 30, and wash compartment 28, respectively. Once a seal is placed along B—B, these compartment portions can become the reagent compartment 22, reaction compartment 26, substrate compartment 30, and wash compartment 28 depicted in FIG. 3. In addition, compartments 102, 104, 106, 108 have removable delivery portions 110, 112, 114, 116, respectively. Further, compartments 102, 104, 106, 108 have fluid input ports 118, 120, 122, 124, respectively. Thus, compartment 102 has a portion that corresponds to binding-reagent compartment 22, a removable delivery portion 110, and a fluid input port 118; compartment 104 has a compartment portion that corresponds to reaction compartment 26, a removable delivery portion 112, and a fluid input port 120; and so forth.

Container 300 can be fabricated as follows. With reference to FIG. 4, an appropriate fluid is inserted into the removable delivery portion through the fluid input port of each compartment. In an immunoassay, for example, a fluid containing at least one binding pair member can be inserted into removable delivery portion 110 of compartment 102; a fluid containing a solid material can be inserted into removable delivery portion 112 of compartment 104; a fluid containing a substrate can be inserted into removable delivery portion 114 of compartment 106; and a wash solution can be inserted into removable delivery portion 116 of compartment 108. After inserting the appropriate fluid into each removable portion, the input port of each compartment can be sealed such that the inserted fluids remain within the compartment. This can be accomplished by heat sealing along reference line A—A. To help minimize the number of bubbles introduced into each compartment, each fluid can be positioned proximal to the compartment portion of each compartment before sealing the fluid input ports. To accomplish this, the container can be positioned such that gravity forces each fluid toward each compartment portion.

After sealing the fluid input ports, at least a portion of each fluid can be moved from the removable delivery portion of each compartment to the compartment portion of each compartment. Again, to help minimize the number of bubbles introduced into each compartment, each fluid can be positioned proximal to the compartment portion of each compartment before moving the fluids. Any process can be used to move the fluids from the delivery portion to the compartment portion. For example, gravity and/or pressure can be used to move the fluid into compartment portion of each compartment. Once at least a portion of each fluid is moved to the compartment portion of a compartment, that portion can be sealed from the delivery portion of each compartment such that the fluid within the compartment portion remains within the compartment portion. For example, a seal can be placed along reference line B—B. The delivering portion of each compartment can then be detached from the container by any suitable means, such as cutting along reference line B—B. In this case, detachment of the delivery portion of each compartment results in a diagnostic device as depicted in FIG. 3.

Figure 5:
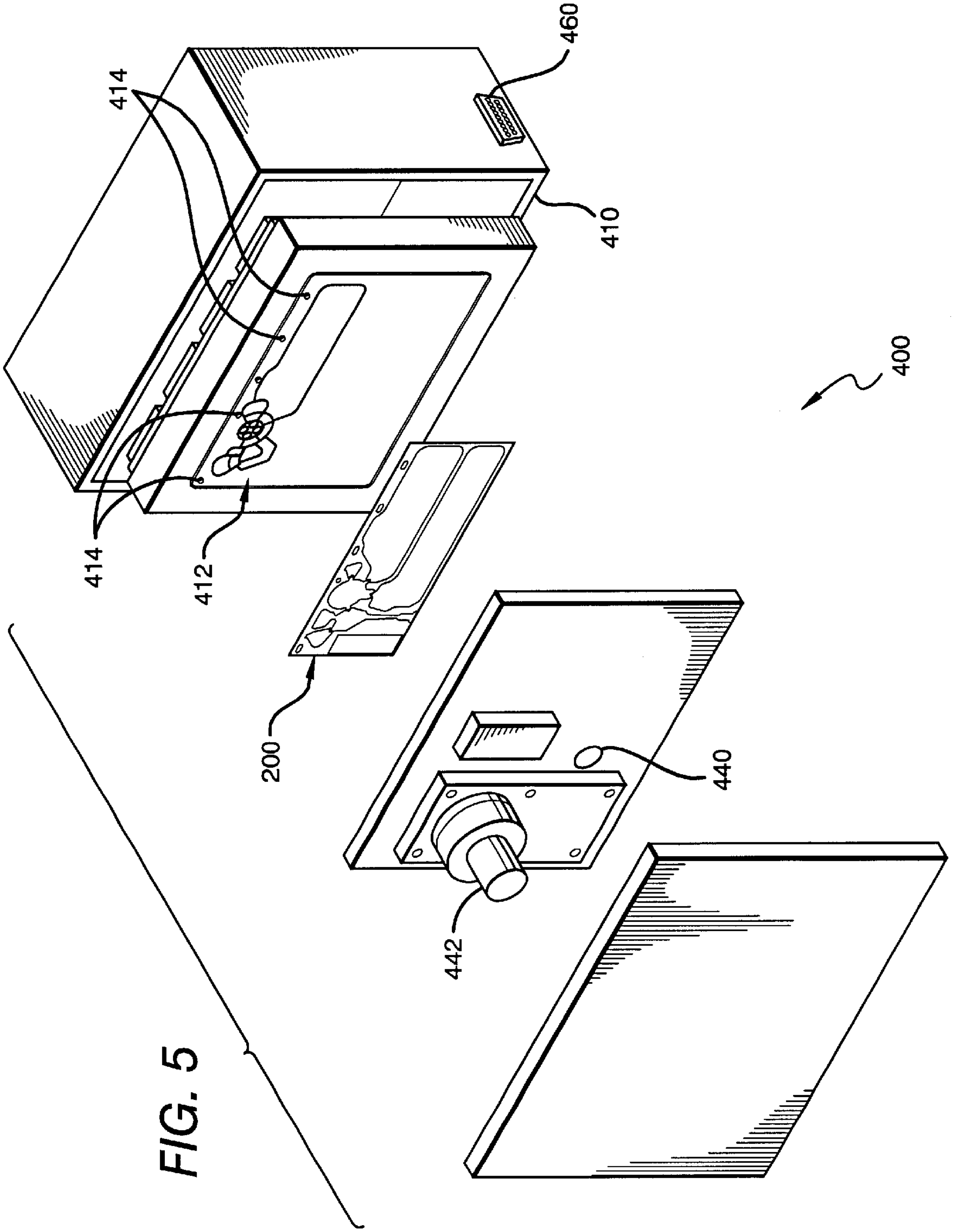
FIG. 5 is a perspective view of an analyzer that cooperates with the containers of FIGS. 1–4 to determine an analyte in a sample.

In FIG. 5 an analyzer 400 generally comprises a main section 410 having a container receiving zone 412 with alignment posts 414, a door 420, multiple actuators 430, a detector 440, a printer 450, and an interface 460. Analyzer 400 is shown with an exemplary workpiece container 200.

The main section 410 houses essentially all of the electronic or other circuitry needed to complete the contemplated tests. Of course, main section 410 can be designed using any suitable shape and dimensions, and can be formed from plastic, metal, or any other suitable materials.

Receiving zone 412 cooperates with door 420 to receive container 10 during the contemplated testing. In alternative embodiments a door is not needed at all, and the container can instead be inserted into an access slot. Alignment posts 414 may be configured in any suitable fashion, and can be eliminated altogether.

Actuator group 412 is used to deliver one or more forces to the container 10, with the object of affecting some material with container 10. Examples of actuators that may form part of group 412 are compression pads, roll bars, or wheels. Contemplated actuators may also have one or more additional functions, including heating, cooling, and delivering a magnetic force. For example, an actuator may heat inactivate an enzyme, or warm a reaction to a desired temperature. In another example, an actuator may be used to concentrate an analyte by binding it the surface of a magnetic bead. Actuators may also be employed to modify a volume occupied by fluids, solids, or air. The fluids may, for example, include a buffer, a sample, a reaction mixture, a reagent solution, etc. The solids may include paramagnetic beads, and the gases may include nitrogen or argon as protective agents, or $CO_2$ as a byproduct of a chemical reaction.

Where an actuator comprises a compression pad, the pad can be made from any material suitable for exerting an appropriate force to a portion of a container, in an appropriate pattern. Typically, a compression pad is a substantially flat surface, and has a shape corresponding to the shape of a compartment or passageway. Where an actuator is employed to otherwise seal a partition, a partitioning edge can be provided, preferably in the form of a wedge or a compression pad having a protrusion.

Detector 440 is essentially one, or any combination of signal detectors used to detect a signal generated through use of the container. Contemplated signal detectors include a photomultiplier tube, a photodiode, and a charge-coupled device. It is optional to include detector 440 in analyzer 400.

Printer 450 is used to print information on any combination of human or machine-readable formats, including printing on a paper label or sheet. It is optional to include a printer in analyzer 400.

Interface 460 can be any type of electronic or other means of exchanging information with another device. A typical interface is a common RS232 (serial) data port.

Not shown are other options for analyzer 400, including a scanner than can detect a bar code, or other hand or machine written information included on a label.

Figure 6:
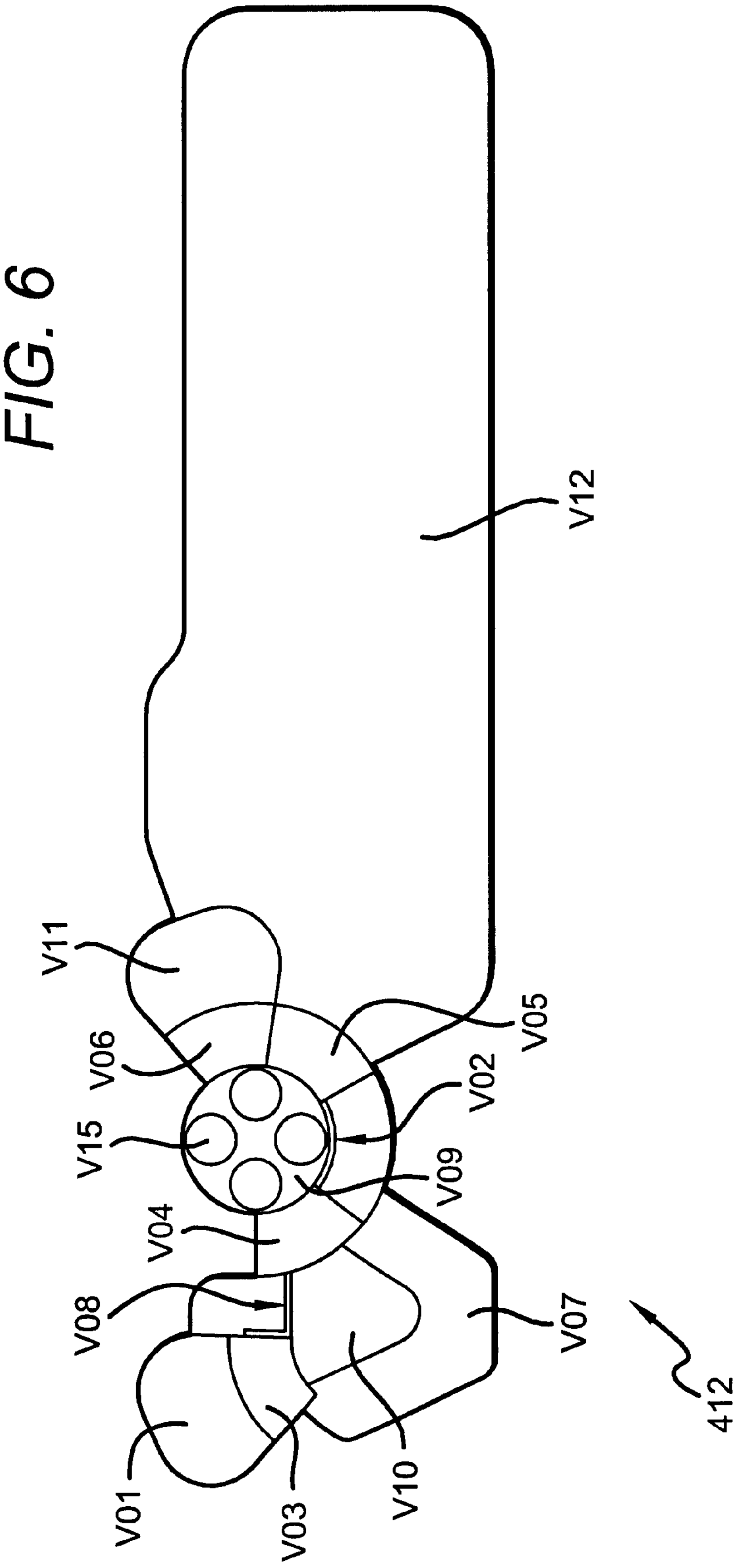
FIG. 6 is a schematic of actuators that can be used in conjunction with the containers of FIGS. 1–4 to determine an analyte in a sample.

FIG. 6 depicts further detail of the actuator group 412 described with respect to FIG. 5, and cooperates with the container 200 of FIG. 3. It should be understood, however, that actuator group 412 could be employed with many different containers besides the specific configuration of container 200, and that a generic actuator group can be employed with a very large number of containers and corresponding test protocols.

With reference to FIG. 6, actuator 412 has a series of compression pads that correspond to the various compartments of a diagnostic device, for example, device 200 depicted in FIG. 3. Each compression pad can serve to apply external force to a particular region of the device such that fluid is moved. For example, a compression pad can be used to apply 5–50 psi of fluid pressure to a chevron break point within a compartment. Typically, two compression pads correspond to each compartment having a chevron break point. One compression pad is used to move fluid toward the chevron break point while the other is used to apply the force to move fluid through the chevron break point. In addition, the compression pad proximal to the chevron break point can be used to prevent movement of fluid between compartments, if necessary.

With reference to FIG. 6, actuator 412 has binding-reagent compartment compression pads V01, V03. Compression of binding-reagent compartment compression pad V01 followed by compression of binding-reagent compartment compression pad V03 can cause a fluid within binding-reagent compartment 22 of device 200 to pass through chevron break point 24 of device 200. In addition, binding-reagent compartment compression pad V03 can serve to prevent movement of fluid between compartments.

Actuator 412 also has volumetric zone compression pads V03, V04, V07, V10. Volumetric zone compression pads V03, V04, V07 can serve to surround partially an area that defines a fixed volume of sample. Volumetric zone compression pad V10 can serve to move a fluid from one compartment to another. In addition, actuator 412 has a partitioning edge V08 that can serve to define a fixed volume. Partitioning edge V08 can prevent fluid from moving between, for example, fluid-receiving portion 18 and overflow portion 20 of device 200.

Actuator 412 also contains a reaction compartment compression pad V09. In addition to being able to move fluid from a reaction compartment, reaction compartment compression pad V09 can rotate such that the magnetic force created by permanent magnet V15 also rotates. A movable magnetic force can be used to move paramagnetic particles within a reaction compartment such that assay kinetics are increased. In addition, a magnetic force provided by permanent or electro-magnet can be used to hold paramagnetic particles in a particular location.

In addition, actuator 412 has substrate compartment compression pads V06, V11; wash compartment compression pads V05, V12; and waste-receiving compartment partitioning edge V02. These compression pads can be used to move fluid while waste-receiving compartment partitioning edge V02 can be used to prevent fluid movement between, for example, reaction compartment 26 and waste-receiving compartment 32 of device 200.

An analyzer apparatus can have any type of signal detection mechanism including, without limitation, a photomultiplier tube, photodiode, and charge-coupled device. With reference to FIG. 5, analyzer apparatus 400 has a photomultiplier tube 414. In addition, shutter 416 can be used to protect photomultiplier tube 414.

The analyzer can be programmable such that the compression pads and partitioning edges apply particular external force at particular times during the diagnostic test. In addition, the analyzer apparatus can have an alignment means (e.g., a plurality of pins) for positioning the diagnostic device. Further, the analyzer can have pressure sensors on either side of each compression pad and partitioning edge. These sensors can be used to determine and regulate the amount of pressure being applied. In addition, these sensors can be used to determine whether each compression pad and partitioning edge is working properly during operation.

The following methods are examples of operations during a test. These methods involve using device 200 with reference to the actuator components depicted in FIG. 6. The number zero (0) means "off" or no external force applied and the number one (1) means "on" or external force applied.

| V01 | V02 | V03 | V04 | V05 | V06 | V07 | V08 | V09 | V10 | V11 | V12 |
|---|---|---|---|---|---|---|---|---|---|---|---|
| To measure a fixed volume of a sample within volumetric zone 20 as a function of time: | | | | | | | | | | | |
| 0 | 1 | 1 | 1 | 1 | 1 | 1 | 0 | 0 | 0 | 0 | 0 |
| 0 | 1 | 1 | 1 | 1 | 1 | 1 | 1 | 0 | 0 | 0 | 0 |
| 0 | 1 | 0 | 1 | 1 | 1 | 1 | 1 | 0 | 0 | 0 | 0 |
| To mix a sample with binding reagent compartment 22, incubate, and mix with magnetic particles within reaction compartment 26: | | | | | | | | | | | |
| 1 | 1 | 0 | 1 | 1 | 1 | 1 | 1 | 0 | 0 | 0 | 0 |
| 1 | 1 | 1 | 1 | 1 | 1 | 1 | 1 | 0 | 0 | 0 | 0 |
| 1 | 1 | 1 | 1 | 1 | 1 | 1 | 1 | 0 | 0 | 0 | 0 |
| 1 | 1 | 1 | 0 | I | 1 | 1 | 1 | 0 | 0 | 0 | 0 |
| 1 | 1 | 1 | 0 | 1 | 1 | 1 | 1 | 0 | 1 | 0 | 0 |
| 1 | 1 | 1 | 1 | 1 | 1 | 1 | 1 | 0 | 1 | 0 | 0 |
| 1 | 1 | 1 | 0 | 1 | 1 | 1 | 1 | 0 | 0 | 0 | 0 |
| 1 | 1 | 1 | 0 | 1 | 1 | 1 | 1 | 1 | 0 | 0 | 0 |
| 1 | 1 | 1 | 0 | 1 | 1 | 1 | 1 | 0 | 0 | 0 | 0 |
| 1 | 1 | 1 | 0 | 1 | 1 | 1 | 1 | 0 | 1 | 0 | 0 |
| 1 | 1 | 1 | 1 | 1 | 1 | 1 | 1 | 0 | 1 | 0 | 0 |
| 1 | 0 | 1 | 1 | 1 | 1 | 1 | 1 | 0 | 1 | 0 | 0 |
| 1 | 0 | 1 | 1 | 1 | 1 | 1 | 1 | 1 | 1 | 0 | 0 |
| To wash the paramagnetic particle: | | | | | | | | | | | |
| 1 | 1 | 1 | 1 | 1 | 1 | 1 | 1 | 0 | 1 | 0 | 0 |
| 1 | 1 | 1 | 1 | 0 | 1 | 1 | 1 | 0 | 1 | 0 | 1 |
| 1 | 1 | 1 | 1 | 1 | 1 | 1 | 1 | 0 | 1 | 0 | 0 |
| 1 | 0 | 1 | 1 | 1 | 1 | 1 | 1 | 0 | 1 | 0 | 0 |
| 1 | 0 | 1 | 1 | 1 | 1 | 1 | 1 | 1 | 1 | 0 | 0 |
| To add substrate from substrate compartment 30: | | | | | | | | | | | |
| 0 | 1 | 0 | 1 | 1 | 0 | 0 | 0 | 0 | 0 | 0 | 0 |
| 0 | 1 | 0 | 1 | 1 | 0 | 0 | 0 | 0 | 0 | 1 | 0 |
| 0 | 1 | 0 | 1 | 1 | 1 | 0 | 0 | 0 | 0 | 1 | 0 |
| 0 | 0 | 0 | 0 | 0 | 0 | 0 | 0 | 0 | 0 | 0 | 0 |

Method of Use

In general, a sample is deposited into inlet port 12 under pressure, and travels to sample compartment 13. Excess sample beyond the capacity of compartment 13 spills over into a spillage compartment 20, which serves to aliquot the amount of sample in compartment 13. A first reactant from compartment 22 is added to the sample, and after appropriate incubation the sample is shunted to reaction compartment 26. Reaction chamber 26 may contain additional reactants, and still further more reactants can be added from substrate or other reactant compartment 30. At one or more points in the processing stage the sample can be washed by a wash fluid from wash compartment 28. Waste material is forced into waste compartment 32. During these processes, various reactions take place with respect to an analyte within the sample, and a color or other detectable signal is produced that corresponds to the amount or existence of analyte. The signal is "read" through one of the side walls of compartment 26.

As used herein, the term "sample" refers to any solid, fluid or gaseous material, which contains at least a portion that can be tested for an analyte. Contemplated solid samples include organic materials, inorganic materials or a mixture of organic materials and inorganic materials. Contemplated organic materials include macromolecules, and assemblies of macromolecules, cells, and tissues. Examples are drugs, viruses, bacterial or eukaryotic cells, and vertebrate tissues. Contemplated inorganic materials include salts, complexes or mixtures thereof, for example, mineral salts and mineral compositions. Liquid samples preferably include water or chemically homogeneous fluids, but may also include mixtures of various liquids with other liquids or components, for example water, petroleum, or coffee. Especially contemplated herein are liquids that comprise complex mixtures of a fluid phase and dissolved or undissolved solids. Examples are bodily fluids, wastewater, beverages and so on. Gaseous samples may include relatively pure gases, but also complex mixtures of relatively pure gases with other gases or vapors.

Examples are ambient air and air with various organic contaminants including $NO_2$, CO, benzene and so forth.

As used herein, the term "analyte" refers to any component in a sample that is to be analyzed. Analytes are generally at least partially soluble in a solvent, or at least miscible in a fluid. Analytes may be an organic, organometallic, inorganic, or any reasonable combination thereof. Contemplated organic compounds range from complex compounds to very simple compounds. For example, analytes of interest include proteins, growth factors, hormones, transmitters, enzymes, clotting factors, IGF-1, bacteria, virus, yeast, acteylcholine, caffeine, benzo(a) pyrene, and dioxin, drugs, calmodulin and Pb-tetraethyl, alkali metal and alkaline earth metal ions such as $K^+$, $Na^+$, $Ca^{2+}$, $Mg^{2+}$, as well as salts.

As used herein, the term "reactant" refers to any composition that can react with a component of a sample, or another reactant, in performing a determination. This includes binding reagents, solid-phases, solvents, wash compositions, signal generators, and so forth. In general, practically any reactant that can be utilized at a lab bench test can also be employed in connection with the containers and devices contemplated herein. Reactants may be contained separately, or in combination, in the various compartments as appropriate for a given test protocol.

One particularly contemplated class of reactants includes test reagents. For example, reactant compartment 22 may contain a fluid that comprises at least one binding pair member. A binding pair member can be any molecule that specifically binds another molecule to form a binding pair, including an antibody or an antigen that specifically binds that antibody. Other contemplated binding pair members include antibody fragments having specific antigen binding capacity, receptors and ligands, sense and anti-sense nucleic acids, metal ions, chelating agents, and aptamers.

In many tests, reagent compartments such as compartment 22 will contain more than one of the reactants for the test being performed, and in the case of assays involving binding, such reactants will often comprise more than one binding pair member. For example, reagent compartment 22 may advantageously contain a first binding pair member and a second binding pair member each having specificity for a different epitope present on an analyte to be detected. In addition, the first binding pair member can be conjugated to a molecule that allows for analyte detection and the second binding pair member can be conjugated to another binding pair member such that an analyte-multiple binding pair member complex can be captured. For example, the fluid within reagent compartment 22 can contain two different antibodies that each bind analyte X present within a sample. The first antibody can be conjugated with an enzyme such that the amount of enzymatic activity can be correlated with the amount of analyte X. The second antibody can be conjugated to biotin such that any complex containing analyte X and the antibodies are captured by streptavidin. It is to be understood that any particular combination of binding pair members can by used to conduct a particular diagnostic test. In another embodiment, a labeled antigen may be used, for example, in competitive assays.

Another contemplated class of reactants includes labels that allow for analyte detection. Once again, as with other aspects of the inventive subject matter, virtually any label that can be employed in a bench test can also be employed in conjunction with the teachings herein. For example, labels can include acridinium esters, isoluminol derivatives, fluorophores, enzymes, and any combination thereof, and enzymes such as alkaline phosphatase, peroxidase, xanthine oxidase, and glucose oxidase can be coupled to a binding pair member to detect the presence of an analyte.

Another contemplated class of reactants includes solid-phase materials, including polypropylene, polyester, polystyrene, polyurethane, nylon, styrene, glass fiber, and thermoplastic. Such solid-phases can be employed in substantially the same manner as employed in ordinary lab procedures. In some classes of tests, for example, a solid-phase may be employed to bind a diagnostically useful compound such as streptavidin. Of special interest are various beads or other particles, and especially paramagnetic particles, which may advantageously be coated with a binding member to bind a target substance. The paramagnetic particles can then be moved under the influence of a magnetic force to separate the bound target substance from the remainder of a sample. A particularly useful application of paramagnetic particles involves the separation of plasma from whole blood. In an exemplary process, whole blood can be combined with a first antibody that has a high specificity for a red blood surface antigen, and subsequently combined with paramagnetic beads to which a second antibody is bound. The second antibody binds to the first antibody, and the red blood cells can be gently pulled away from the remaining plasma under the influence of a magnetic field.

It is specifically contemplated that a solid phase may be moved from one compartment to another. Beads may be moved in that manner, as can a "puck" that alters fluid flows within or between compartments.

Reactants may also comprise a solvent or other simple fluid. The fluid may be used for many purposes, including maintaining the stability of a reactant, or to fluidize a substance that would otherwise be in a solid state, or for use as a wash. Contemplated fluids for these purposes include preservatives, detergents (e.g. CHAPS, Tween-20, Triton X-100, cholate, and SDS), proteins (e.g. BSA), saline, phosphate-buffered saline, tris-buffered saline, water, and compatible aqueous organic solvents.

Another particularly contemplated class of reactants is a filter material. All of the known filter materials are contemplated, including nitrocellulose, steel wool, and so forth.

A very large number of test protocols can be accomplished in accordance with the teaching principles set forth herein. In addition to the tests referred to herein, multiple tests can be run on a single sample by aliquoting portions of the sample to multiple reaction chambers, and additional compartments can be added to accommodate additional reagents. Agitation, heating and other operations can be accomplished by the appropriate actuators, and time delays of anywhere from a fraction of a second, to one or more minutes can readily be accommodated. Thus, the teachings herein should not be read as limiting the application to any particular assay or protocol, or to any particular container or detector.

EXAMPLE

Diagnostic Assay

With respect to FIG. 1, an operator selects a container 10 adapter for an appropriate test, and inserts a 100 $\mu$L sample (calibrator, controls, or patient samples) into entry port 12. The sample passes under pressure to compartment 13.

The container 10 is then placed in an analyzer 400, and employing various actuators the analyzer 400 takes control of the testing protocol. First, passageway 16 is sealed, preferably by a sealing actuator compressing the opposing top and bottom sheets of the container 10 at appropriate places. Compartment 18 is then squeezed to aliquot a specific desired volume of sample, with excess sample passing into compartment 20. The connection between compartments 18 and 20 is then actuator sealed.

Using another actuator, 100 $\mu$L of an antibody solution containing biotinylated monoclonal anti-PSA antibody and polyclonal alkaline phosphatase-labeled antibody is passed from compartment 22 into compartment 14. After addition of the antibody solution, the sample is incubated for 5 minutes at 37° C.

Using another actuator the sample is passed to compartment 26, in which was stored 25 μL–100 μL of a homogenous suspension of streptavidin-coated paramagnetic particles. Using one or more actuators, a shaking or vibrating motion is imparted to the sample, and further incubation takes place for an interval, such as 2 minutes at 37° C.

Using other actuators, about 1.0 ml of a wash solution is passed from wash compartment 28 into compartment 26 to wash the sample. Further incubation is allowed to take place, during which the paramagnetic particles sediment. Sedimentation may be enhanced using a magnetic force from a permanent magnet.

Using other actuators, about 50 μL–100 μL of a chemiluminogenic substrate (ImmuGlow) is added to compartment 26 from compartment 30.

Using other actuators, about 100 μL–300 μL of wash is added to the sample in compartment 26 from compartment 31, and agitated for several seconds. The wash cycle is repeated three to four times.

Chemiluminescence is measured after a specified interval, for example, 15 seconds following addition of the substrate. Determination of the unknown is computed using a standard-dose-response curve. Depending on the test, additional measurements can be made at intervals, such as a minute or longer.

Thus, specific embodiments and applications of methods and apparatus for performing tests have been disclosed. It should be apparent, however, to those skilled in the art that many more modifications besides those already described are possible without departing from the inventive concepts herein. The inventive subject matter, therefore, is not to be restricted except in the spirit of the appended claims.

What is claimed is:

1. A method of testing a sample for a analyte, comprising:

providing a container having a plurality of fluidly discontinuous compartments, including a sample reacting compartent, different first and second reagents contained in first and second reagent compartments, respectively, and a signal detection compartment;

receiving the sample into the sample reacting compartment;

contacting a surface of the container with a device having a plurality of actuators;

operating multiple different sets of the actuators to independently add the first and second reagents to the sample in a variable sequence and time delay;

moving at least a portion of the reacted sample between the sample reacting compartment and the sample detection compartment using at least one of the sets of actuators; and reading an analyte-dependent signal from the reacted sample contained in the sample detection compartment.

2. The method of claim 1, wherein the container has a flexible top sheet and a flexible bottom sheet, and wherein at least one of the compartments is formed by the flexible top sheet and bottom sheet.

3. The method of claim 1, further comprising aliquoting the sample.

4. The method of claim 1, wherein the step of receiving the sample comprises diluting the sample.

5. The method of claim 1, wherein the step of operating the actuators comprises contacting at least a portion of the sample with a composition having a substantially selective binding towards the analyte.

6. The method of claim 1, wherein the step of operating the actuators comprises contacting at least a portion of the sample with a composition selected from the group consisting of nucleic acids, antibodies, antigens, solid-phases, substrates, wash solutions, and buffers.

7. The method of claim 1, wherein the step of operating the actuators comprises aliquoting the sample, contacting at least a portion of the sample with a composition having a substantially selective binding towards the analyte, and contacting at least a portion of the sample with a reagent selected from the group consisting of a solid-phase, a wash solution, and a substrate.

8. The method of claim 1, wherein at least a portion of the sample is reversibly moved between the sample reacting compartment and the sample detecting compartment.

9. The method of claim 1, further comprising receiving the sample into a sample receiving compartment distinct form the sample reacting compartment.

10. The method of claim 1, wherein the fit and second reagents can be added to the sample in any variable sequence.

11. The method of claim 1, wherein the first reagent is selected from the group consisting of antibody, nucleic acids, chromophore, and amplifier.

12. The method of claim 1, wherein at least one of the actuators comprises a compression pad.

13. The method of any of claims 1–12, further comprising providing the device with a signal detector, and detecting the signal using the signal detector.

14. The method of claim 13, wherein detecting the signal using the signal detector comprises detecting multiple events separated by at least one minute.

15. The method of claim 13, wherein detecting the signal is performed at more than one of the compartments.

16. The method of claim 13, wherein the signal detector is selected from the group consisting of a photomultiplier tube, a photodiode, and a charge-coupled device.

17. The method of any of claims 1–12, further comprising the device calculating a result using the signal.

18. The method of any of claims 1–12, further comprising providing the device with an onboard printer, and printing an output relating to the result.

19. The method of any of claims 1–12, further comprising providing the device with an electronic interface to an external device, and sending an output relating to the result through the interface.

20. The method of any of claims 1–12, further comprising washing the sample, with a waste fluid passing into a waste compartment.

21. The method of claim 1 wherein the signal is dependent on the concentration of the analyte.

22. The method of claim 1 wherein the step of reacting further comprises washing complex formed between the analyte and at least one of the first reagent and second reagents.

* * * * *